(12) United States Patent  (10) Patent No.: US 7,771,444 B2
Patel et al.  (45) Date of Patent: *Aug. 10, 2010

(54) METHODS AND DEVICES FOR REMOVING MATERIAL FROM A BODY LUMEN

(75) Inventors: Himanshu Patel, San Jose, CA (US); John B. Simpson, Woodside, CA (US); Darren G. Doud, San Jose, CA (US)

(73) Assignee: Fox Hollow Technologies, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/027,418

(22) Filed: Dec. 19, 2001

(65) Prior Publication Data

US 2002/0077642 A1 Jun. 20, 2002

Related U.S. Application Data

(60) Provisional application No. 60/272,273, filed on Feb. 27, 2001, provisional application No. 60/257,704, filed on Dec. 20, 2000.

(51) Int. Cl.
*A61B 17/22* (2006.01)
(52) U.S. Cl. .................. 606/159; 606/167; 606/170
(58) Field of Classification Search .............. 606/159, 606/170, 167, 171, 180; 600/564
See application file for complete search history.

(56) References Cited

U.S. PATENT DOCUMENTS

| 2,178,790 | A | 11/1939 | Henry |
| 3,705,577 | A | 12/1972 | Sierra |
| 3,815,604 | A | 6/1974 | O'Malley et al. |
| 3,831,585 | A | 8/1974 | Brondy et al. |
| 3,837,345 | A | 9/1974 | Matar |
| 3,995,619 | A | 12/1976 | Glatzer |
| 4,210,146 | A | 7/1980 | Banko |
| 4,669,469 | A | 6/1987 | Gifford et al. |
| 4,696,298 | A | 9/1987 | Higgins et al. |
| 4,771,774 | A | 9/1988 | Simpson et al. |

(Continued)

FOREIGN PATENT DOCUMENTS

DE 93 03 531 U1 7/1994

(Continued)

OTHER PUBLICATIONS

Brezinski et al., "Optical Coherence Tomography for Optical Biopsy," Circulation, 93:1206-1213 (1996).

(Continued)

*Primary Examiner*—Darwin P Erezo
(74) *Attorney, Agent, or Firm*—Popovich, Wiles & O'Connell, P.A.

(57) ABSTRACT

A debulking catheter comprising a debulking assembly for debulking a body lumen. The catheters of the present invention can include a flexible proximal portion coupled to a rigid distal portion. A tissue debulking assembly can be disposed within the rigid portion to debulk the body lumen. In exemplary embodiments, the rigid portion is rotatably coupled to the flexible portion such that rotation or deflection of the rigid portion, relative to the flexible portion, can expose the tissue debulking assembly through a window in the catheter to debulk the body lumen.

7 Claims, 15 Drawing Sheets

U.S. PATENT DOCUMENTS

| | | | |
|---|---|---|---|
| 4,781,186 A | 11/1988 | Simpson et al. | |
| 4,817,613 A | 4/1989 | Jaraczewski et al. | |
| 4,819,635 A | 4/1989 | Shapiro | |
| 4,850,957 A | 7/1989 | Summers | |
| 4,886,061 A * | 12/1989 | Fischell et al. | 606/159 |
| 4,926,858 A | 5/1990 | Gifford, III et al. | |
| RE33,258 E | 7/1990 | Onik et al. | |
| 4,966,604 A * | 10/1990 | Reiss | 606/159 |
| 4,979,951 A | 12/1990 | Simpson | |
| 4,986,807 A * | 1/1991 | Farr | 606/159 |
| 4,994,067 A | 2/1991 | Summers | |
| 5,000,185 A | 3/1991 | Yock | |
| 5,024,234 A * | 6/1991 | Leary et al. | 600/467 |
| 5,024,651 A | 6/1991 | Shiber | |
| 5,047,040 A | 9/1991 | Simpson et al. | |
| 5,053,044 A * | 10/1991 | Mueller et al. | 606/159 |
| 5,054,492 A | 10/1991 | Scribner et al. | |
| 5,071,425 A | 12/1991 | Gifford et al. | |
| 5,084,010 A | 1/1992 | Plaia et al. | |
| 5,085,662 A * | 2/1992 | Willard | 606/159 |
| 5,087,265 A | 2/1992 | Summers | |
| 5,092,873 A | 3/1992 | Simpson et al. | |
| 5,114,399 A | 5/1992 | Kovalcheck | |
| 5,154,724 A * | 10/1992 | Andrews | 606/159 |
| 5,181,920 A | 1/1993 | Mueller et al. | |
| 5,217,474 A * | 6/1993 | Zacca et al. | 606/159 |
| 5,222,966 A | 6/1993 | Perkins et al. | |
| 5,224,488 A | 7/1993 | Neuffer | |
| 5,224,949 A | 7/1993 | Gomringer et al. | |
| 5,226,909 A | 7/1993 | Evans et al. | |
| 5,226,910 A | 7/1993 | Kajiyama et al. | |
| 5,242,460 A | 9/1993 | Klein et al. | |
| 5,250,059 A | 10/1993 | Andreas et al. | |
| 5,250,065 A | 10/1993 | Clement et al. | |
| 5,269,793 A | 12/1993 | Simpson et al. | |
| 5,282,484 A * | 2/1994 | Reger | 128/898 |
| 5,285,795 A | 2/1994 | Ryan et al. | |
| 5,312,425 A * | 5/1994 | Evans et al. | 606/159 |
| 5,318,032 A | 6/1994 | Lonsbury et al. | |
| 5,318,528 A | 6/1994 | Heaven et al. | |
| 5,321,501 A | 6/1994 | Swanson et al. | |
| 5,370,651 A * | 12/1994 | Summers | 606/159 |
| 5,372,601 A | 12/1994 | Lary | |
| 5,372,602 A | 12/1994 | Burke | |
| 5,395,313 A | 3/1995 | Naves et al. | |
| 5,403,334 A | 4/1995 | Evans et al. | |
| 5,419,774 A | 5/1995 | Willard et al. | |
| 5,429,136 A * | 7/1995 | Milo et al. | 600/439 |
| 5,431,673 A | 7/1995 | Summers et al. | |
| 5,441,510 A | 8/1995 | Simpson et al. | |
| 5,459,570 A | 10/1995 | Swanson et al. | |
| 5,470,415 A | 11/1995 | Perkins et al. | |
| 5,485,042 A | 1/1996 | Burke et al. | |
| 5,491,524 A | 2/1996 | Hellmuth et al. | |
| 5,505,210 A | 4/1996 | Clement | |
| 5,507,292 A | 4/1996 | Jang et al. | |
| 5,507,760 A | 4/1996 | Wynne et al. | |
| 5,507,795 A | 4/1996 | Chiang et al. | |
| 5,514,115 A | 5/1996 | Frantzen et al. | |
| 5,527,325 A | 6/1996 | Conley et al. | |
| 5,549,601 A | 8/1996 | McIntyre et al. | |
| 5,569,277 A | 10/1996 | Evans et al. | |
| 5,571,122 A | 11/1996 | Kelly et al. | |
| 5,571,130 A | 11/1996 | Simpson et al. | |
| 5,584,842 A | 12/1996 | Fogarty et al. | |
| 5,620,447 A | 4/1997 | Smith et al. | |
| 5,624,457 A | 4/1997 | Farley et al. | |
| 5,626,562 A * | 5/1997 | Castro | 604/508 |
| 5,632,754 A | 5/1997 | Farley et al. | |
| 5,634,464 A | 6/1997 | Jang et al. | |
| 5,643,296 A * | 7/1997 | Hundertmark et al. | 606/159 |
| 5,643,298 A * | 7/1997 | Nordgren et al. | 606/159 |
| 5,665,098 A | 9/1997 | Kelly et al. | |
| 5,669,920 A | 9/1997 | Conley et al. | |
| 5,674,232 A | 10/1997 | Halliburton | |
| 5,695,506 A | 12/1997 | Pike | |
| 5,700,687 A | 12/1997 | Finn | |
| 5,709,698 A | 1/1998 | Adams et al. | |
| 5,733,296 A | 3/1998 | Rogers et al. | |
| 5,741,270 A | 4/1998 | Hansen et al. | |
| 5,776,114 A | 7/1998 | Frantzen et al. | |
| 5,816,923 A | 10/1998 | Milo et al. | |
| 5,823,971 A | 10/1998 | Robinson et al. | |
| 5,830,224 A | 11/1998 | Cohn et al. | |
| 5,836,957 A | 11/1998 | Schulz et al. | |
| 5,843,103 A | 12/1998 | Wulfman | |
| 5,868,685 A | 2/1999 | Powell et al. | |
| 5,868,767 A | 2/1999 | Farley et al. | |
| 5,883,458 A | 3/1999 | Sumita et al. | |
| 5,895,402 A * | 4/1999 | Hundertmark et al. | 606/171 |
| 5,911,734 A * | 6/1999 | Tsugita et al. | 606/200 |
| 5,916,210 A | 6/1999 | Winston | |
| 5,938,671 A | 8/1999 | Katoh et al. | |
| 5,941,869 A * | 8/1999 | Patterson et al. | 604/508 |
| 5,948,184 A | 9/1999 | Frantzen et al. | |
| 5,951,482 A | 9/1999 | Winston et al. | |
| 5,954,745 A * | 9/1999 | Gertler et al. | 606/200 |
| 5,968,064 A | 10/1999 | Selmon et al. | |
| 5,989,281 A * | 11/1999 | Barbut et al. | 606/200 |
| 6,010,449 A | 1/2000 | Selmon et al. | |
| 6,013,072 A | 1/2000 | Winston et al. | |
| 6,022,362 A | 2/2000 | Lee et al. | |
| 6,027,450 A | 2/2000 | Brown et al. | |
| 6,027,514 A | 2/2000 | Stine et al. | |
| 6,036,656 A | 3/2000 | Slater | |
| 6,036,707 A | 3/2000 | Spaulding | |
| 6,048,349 A | 4/2000 | Winston et al. | |
| 6,063,093 A | 5/2000 | Winston et al. | |
| 6,068,638 A | 5/2000 | Makower | |
| 6,081,738 A | 6/2000 | Hinohara et al. | |
| 6,099,542 A | 8/2000 | Cohn et al. | |
| 6,106,515 A | 8/2000 | Winston et al. | |
| 6,120,515 A | 9/2000 | Rogers et al. | |
| 6,120,516 A | 9/2000 | Selmon et al. | |
| 6,126,649 A | 10/2000 | VanTassel et al. | |
| 6,134,003 A | 10/2000 | Tearney et al. | |
| 6,157,852 A | 12/2000 | Selmon et al. | |
| 6,159,225 A | 12/2000 | Makower | |
| 6,183,432 B1 | 2/2001 | Milo | |
| 6,190,353 B1 * | 2/2001 | Makower et al. | 604/95.01 |
| 6,191,862 B1 | 2/2001 | Swanson et al. | |
| 6,193,676 B1 | 2/2001 | Winston et al. | |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,228,076 B1 | 5/2001 | Winston et al. | |
| 6,231,546 B1 | 5/2001 | Milo et al. | |
| 6,235,000 B1 | 5/2001 | Milo et al. | |
| 6,241,667 B1 | 6/2001 | Vetter et al. | |
| 6,241,744 B1 | 6/2001 | Imran et al. | |
| 6,258,052 B1 | 7/2001 | Milo | |
| 6,266,550 B1 | 7/2001 | Selmon et al. | |
| 6,283,951 B1 | 9/2001 | Flaherty et al. | |
| 6,283,983 B1 | 9/2001 | Makower et al. | |
| 6,299,622 B1 | 10/2001 | Snow et al. | |
| 6,302,875 B1 | 10/2001 | Makower et al. | |
| 6,330,884 B1 | 12/2001 | Kim | |
| 6,355,005 B1 | 3/2002 | Powell et al. | |
| 6,375,615 B1 | 4/2002 | Flaherty et al. | |
| 6,394,976 B1 | 5/2002 | Winston et al. | |
| 6,398,798 B2 | 6/2002 | Selmon et al. | |
| 6,428,552 B1 | 8/2002 | Sparks | |
| 6,443,966 B1 * | 9/2002 | Shiu | 606/159 |
| 6,445,939 B1 | 9/2002 | Swanson et al. | |

| | | | |
|---|---|---|---|
| 6,447,525 B2 | 9/2002 | Follmer et al. | |
| 6,475,226 B1 * | 11/2002 | Belef et al. | 606/185 |
| 6,623,496 B2 | 9/2003 | Snow et al. | |
| 6,638,233 B2 * | 10/2003 | Corvi et al. | 600/564 |
| 6,997,934 B2 * | 2/2006 | Snow et al. | 606/159 |
| 7,318,831 B2 | 1/2008 | Alvarez et al. | |
| 2002/0022788 A1 | 2/2002 | Corvi et al. | |
| 2003/0018346 A1 | 1/2003 | Follmer et al. | |
| 2003/0120295 A1 | 6/2003 | Simpson et al. | |
| 2003/0125757 A1 | 7/2003 | Patel et al. | |
| 2003/0125758 A1 | 7/2003 | Simpson et al. | |
| 2004/0167553 A1 | 8/2004 | Simpson et al. | |
| 2004/0167554 A1 | 8/2004 | Simpson et al. | |
| 2005/0222663 A1 | 10/2005 | Simpson et al. | |
| 2007/0010840 A1 | 1/2007 | Rosenthal et al. | |
| 2007/0276419 A1 | 11/2007 | Rosenthal | |

FOREIGN PATENT DOCUMENTS

| | | |
|---|---|---|
| DE | 44 44 166 A1 | 6/1996 |
| WO | WO 02/45598 A2 | 6/2002 |

OTHER PUBLICATIONS

Brezinski et al., "Assessing Atherosclerotic Plaque Morphology: Comparison of Optical Coherence Tomography and High Frequency Intravascular Ultrasound," Heart, 77:397-403 (1997).

Huang et al., "Optical Coherence Tomography," Science, 254:1178-1181 (1991).

International Search Report and Written Opinion of PCT Application No. PCT/US04/12600, dated Jun. 13, 2008, 8 pages total.

International Search Report of PCT Application No. PCT/US04/12601, dated Jun. 30, 2005, 3 pages total.

U.S. Appl. No. 10/288,559, filed Nov. 4, 2002, Himanshu Patel et al. (59 pages).

U.S. Appl. No. 10/421,980, filed Apr. 22, 2003, John B. Simpson et al. (36 pages).

U.S. Appl. No. 10/288,582, filed Nov. 4, 2002, John B. Simpson et al. (48 pages).

U.S. Appl. No. 12/431,210, filed Apr. 28, 2009, John B. Simpson et al. (59 pages).

U.S. Appl. No. 09/378,224, filed Aug. 19, 1999 entitled *Atherectomy Catheter with Aligned Imager*.

U.S. Appl. No. 09/377,884, filed Aug. 19, 1999 entitled *Apparatus and Methods for Material Capture and Removal*.

Abstract of DE 44 44 166 A1 (1 page), (1996).

Mar. 27, 2009 Communication from the European Patent Office regarding corresponding EP Application No. 01 991 343.3 (7 pages).

* cited by examiner

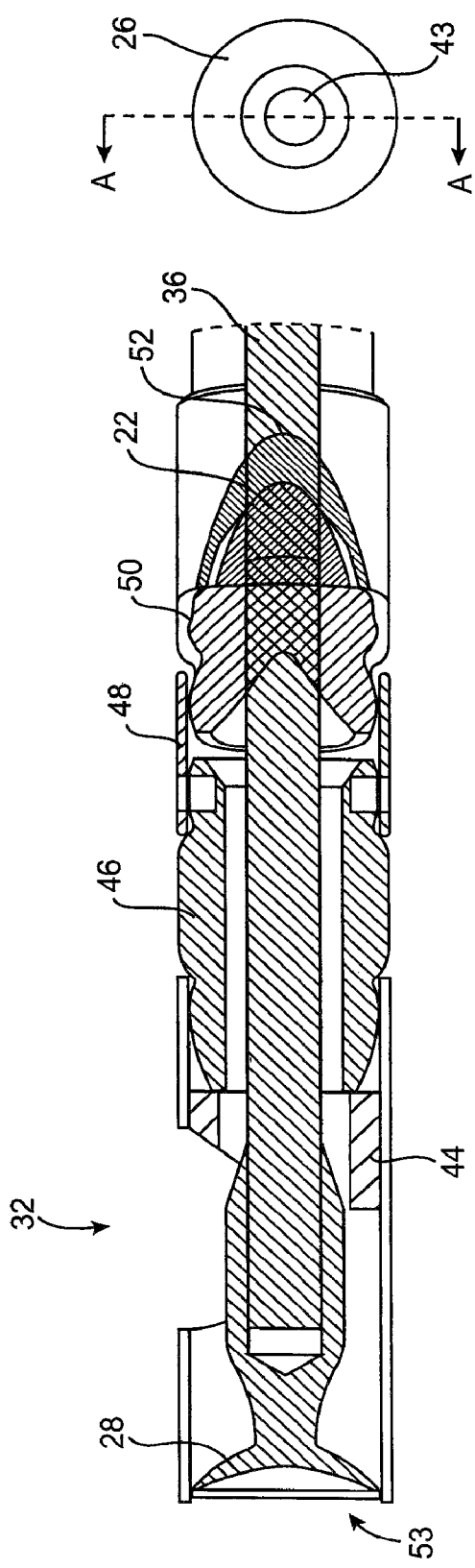

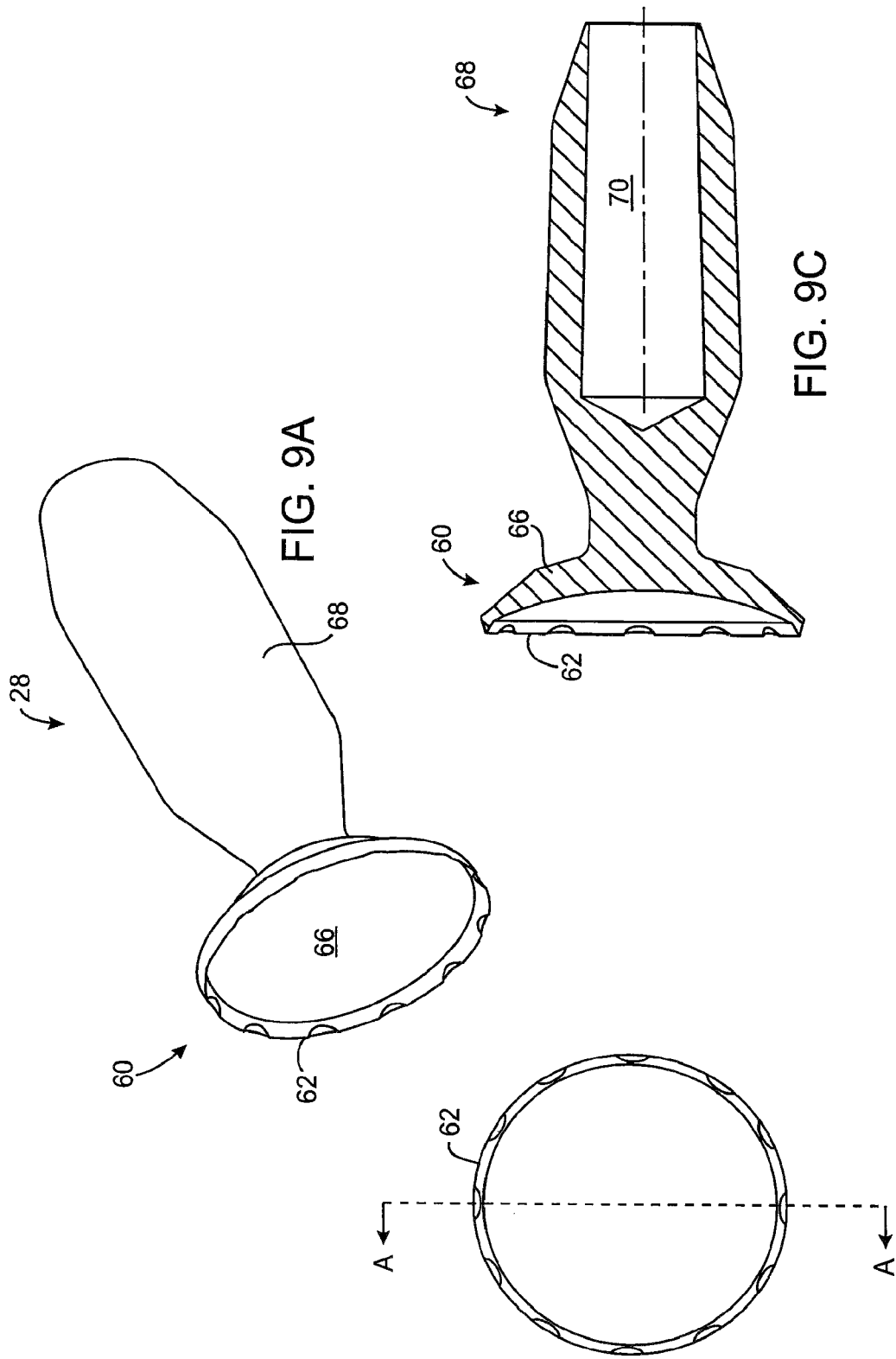

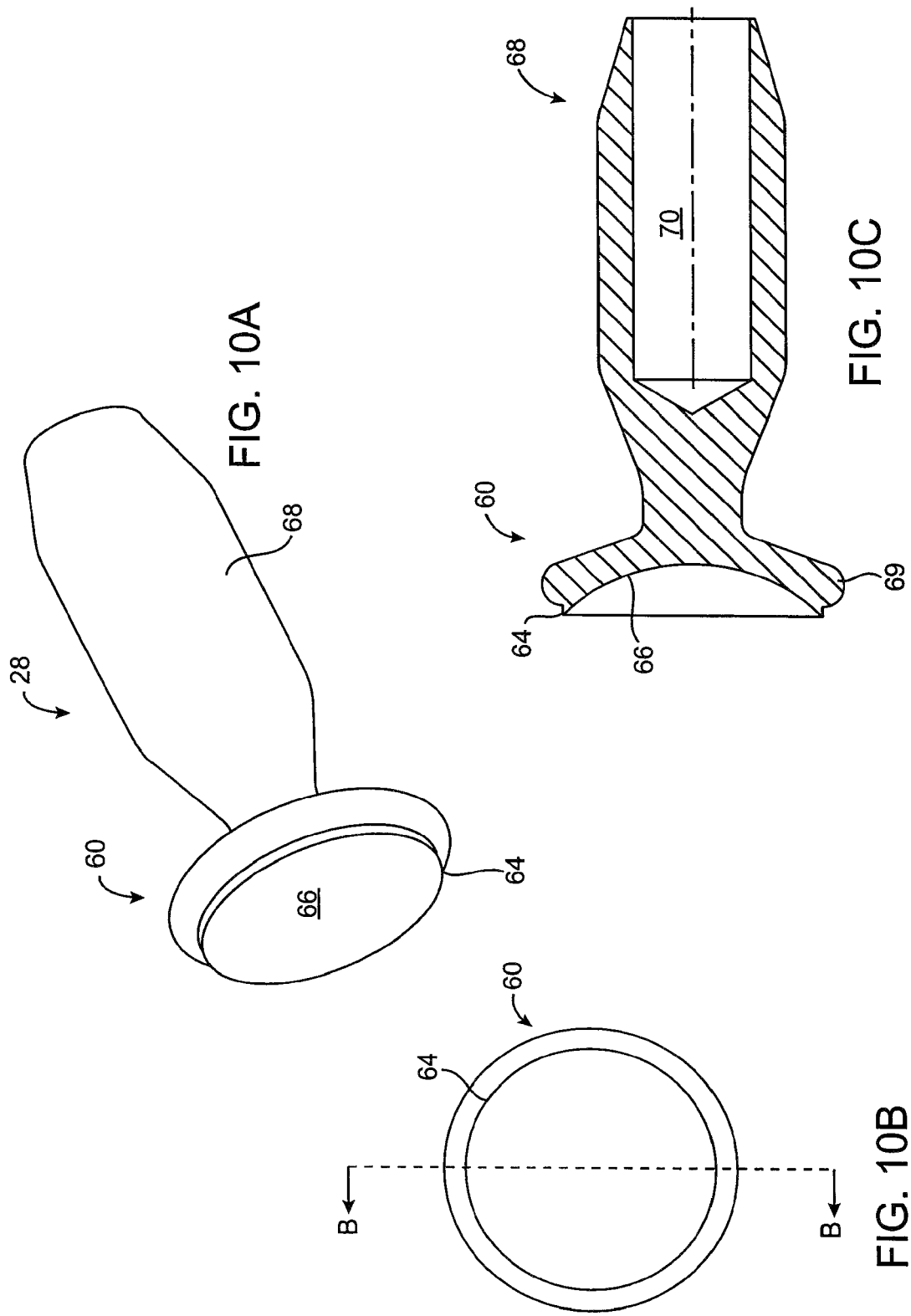

METHODS AND DEVICES FOR REMOVING MATERIAL FROM A BODY LUMEN

CROSS-REFERENCES TO RELATED APPLICATIONS

The present invention claims benefit of Provisional Patent Application Ser. No. 60/257,704, filed Dec. 20, 2000, entitled "Debulking Catheter" and Provisional Patent Application Ser. No. 60/272,273 filed Feb. 27, 2001, the complete disclosures of which are incorporated herein by reference.

The present invention is also related to U.S. patent application Ser. No. 09/377,884, filed Aug. 19, 1999, now U.S. Pat. No. 6,638,233, entitled "Apparatus and Methods for Material Capture and Removal" and Ser. No. 09/377,894, filed Aug. 19, 1999, now U.S. Pat. No. 6,447,525, entitled "Apparatus and Methods for Removing Material From a Body Lumen," the complete disclosures of which are incorporated by reference.

BACKGROUND OF THE INVENTION

The present invention relates generally to systems and methods for debulking body lumens. More particularly, the present invention relates to atherectomy catheters for excising atheroma and other materials from blood vessels and from stents.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

One conventional treatment for cardiovascular disease is the use of stents. Endoluminal stents are commonly used to treat obstructed or weakened body lumens, such as blood vessels and other vascular lumens. Once deployed in the blood vessel, the stent can remain in the body lumen where it will maintain the patency of the lumen and/or support the walls of the lumen which surround it. One factor impeding the success of stent technology in endoluminal treatments is the frequent occurrence of in-stent restenosis, characterized by proliferation and migration of smooth muscle cells within and/or adjacent to the implanted stent, causing reclosure or blockage of the body lumen.

Atherosclerosis and restenosis can be treated in a variety of ways, including drugs, bypass surgery, and a variety of catheter-based approaches which rely on intravascular debulking or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon to urge the aperture against the material to be removed.

Although atherectomy catheters have proven to be very successful in treating many types of atherosclerosis and in-stent restenosis, conventional catheter designs suffer from certain limitations. For example, many side-cutting atherectomy catheters have difficulty in capturing occluding material in the cutting aperture. To facilitate material capture the cutting aperture is frequently elongated to increase the area into which the material can penetrate. While such elongation is effective, it requires an equivalent lengthening of the cutter housing. Since most cutter housings are rigid such lengthening makes it more difficult to introduce the distal end of the catheter through tortuous regions of the vasculature. Moreover, conventional atherectomy catheters typically require a balloon positioned opposite the cutting window to urge the material into the cutting window. Such balloons however, unduly increase the size of the distal portion of the catheter. Even with the balloon, the amount of material that can be removed by conventional atherectomy catheters is limited by the size of the cutting window.

For these reasons, it is desired to provide atherectomy catheters which can access small, tortuous regions of the vasculature and which can remove atheromatous and other occluding materials from within blood vessels and stents in a controlled fashion. In particular, it is desired to provide atherectomy catheters which can facilitate capturing and invaginating atheromatous materials. The catheters and methods for use in a variety of body lumens, including but not limited to coronary and other arteries. At least some of these objectives will be met by the catheter and method of the present invention described hereinafter and in the claims.

BRIEF SUMMARY OF THE INVENTION

The present invention provides catheters, kits, and methods for debulking a body lumen. The catheters and methods of the present invention are for use in a variety of body lumens, including but not limited to intravascular lumens such as the coronary artery and other blood vessels.

In one aspect, the catheters of the present invention can include a flexible proximal portion coupled to a rigid distal portion. A tissue debulking assembly can be disposed within the rigid portion to debulk the body lumen. In exemplary embodiments, the rigid portion is rotatably coupled to the flexible portion such that rotation or deflection of the rigid portion, relative to the flexible portion, can expose the tissue debulking assembly through a window in the catheter to debulk the body lumen.

In exemplary embodiments, movement of the debulking assembly causes the deflection of the distal portion. For example, movement of the debulking assembly from a distal position to a proximal position can cause the distal portion to deflect and cause the debulking assembly to move outside of the window, beyond an outer diameter of the catheter body.

The rigid distal portion of the catheter can be rotatably coupled to a flexible portion of a catheter through a connection assembly, such as one or more articulation members, pivot pins, one or more flexible joints, or the like. A longitudinal axis of the distal portion of the catheter body will be angled or offset from a longitudinal axis of the cutter and the rest of the catheter when it is deflected from the proximal portion of the catheter. The deflection of the distal portion of the catheter body to an angled or offset configuration relative to the rest of the catheter body can urge the distal portion against the body lumen so as to bias the debulking assembly against an opposite side of the lumen wall. Because the deflection of the distal portion can increase the profile of the catheter and bias the debulking assembly against the body lumen without the use of a balloon, and because the debulking assembly can be exposed outside of the window beyond a diameter of the distal portion such that the target tissue does not have to invaginate the window, the rigid portion of the catheter and the window can be decreased in size (both longitudinally and radially) so as to allow the catheters to reach the tortuous and smaller diameter body lumens and to reduce the trauma to the body lumen (e.g., barotrauma of balloons) during advancement to the target site. In exemplary embodiments, the distal portion of the catheter includes a rigid housing that has a rigid length of approximately 6 mm to 8 mm.

The tissue debulking assembly can take a variety of forms. In exemplary embodiments, the tissue debulking assembly is a movable, rotatable cutter having a serrated or smooth edged cutting blade. The rotatable cutter is typically coupled to a drive shaft and a driver, such that actuation of the driver with an input device can activate movement and/or rotation of the cutter. In such embodiments the cutter can automatically rotate as the cutter is moved out of the cutting window. Advantageously, the user will only have to activate a single switch or handle to activate the cutter, bias the cutter against the material to be removed, and to activate the spinning of the cutter.

Depending on the type of occlusion in the body lumen, certain cutter designs are more effective than other cutter designs. In a specific embodiment, the cutter can include a serrated blade. In other embodiments, the cutter can include a non-serrated blade that has been found to be more effective in removing in-stent restenosis. Optionally, the in-stent restenosis cutter can include a bump along its edge to reduce the cutting edge interaction with the stent.

It should be appreciated however, that the present invention is not limited to cutter debulking assemblies. In other embodiments, instead of a cutter, the tissue debulking assembly can be a movable or stationary RF electrode, laser, ultrasound emitter, grinder, or the like.

The deflection of the distal portion of the catheter is typically caused by actuation of an input device. For example, the input device can control the movement of the debulking assembly between a first and second position. When the debulking assembly is in a first position it will be disposed within the catheter. Movement of the tissue debulking assembly from a first position to a second position causes the rotation/deflection of the rigid portion relative to the flexible portion and exposes the tissue debulking assembly through the window. Thereafter, the entire catheter body can be advanced through the body lumen to debulk the body lumen with the exposed debulking assembly.

In some embodiments, the cutter is exposed through the window by contacting the cutter with cams or ramps on the distal portion of the catheter as the cutter is moved proximally across the window. Interaction of the cutter with the cams urges the distal portion of the catheter out of alignment with the cutter and proximal portion of the catheter and exposes the cutter through the window. Typically, the cutter is moved out of the window beyond an outer diameter of the catheter body to debulk the target tissue. As the cutter is moved distally, the cutter will move back into the window and lose engagement with the cams, and the distal portion of the catheter will move back into alignment with the rest of the catheter body. Such movement of the distal portion will align the cutter with the tip such that the severed material can be directed into a collection chamber in the distal tip.

In some embodiments, a flexible distal tip can be attached to the rigid distal portion of the catheter. The distal tip may be removably or integrally attached to the distal portion of the catheter. By integrating the tip with the distal portion of the catheter body, the joint between the tip and catheter body is eliminated, thus providing a continuous inner diameter from the housing to the tip which results in improved tissue packing. In some embodiments, the distal tip has a reducing stiffness in the distal direction. The gradual change in stiffness results in the elimination of a rigid joint and the decreasing stiffness of the tip can provide better access to tortuous vessels, while being less traumatic to the vessel wall. In other embodiments, however, the flexible distal tip may have a constant flexibility throughout its length.

In other embodiments, the catheter can include a fixed wire tip. The fixed wire tip can be used to advance the catheter through the body lumen without the use of a separate guidewire. In yet other embodiments, the distal tip is blunted to provide for atraumatic advancement through the body lumen. In one arrangement, the blunt tip can be stiff enough to allow for advancement of the catheter without the use of a guidewire. In an alternative arrangement, the blunt tip will have a lumen that can receive a guidewire.

Some embodiments of the catheter include a distal tip that facilitates rapid exchange of a guidewire. The distal tip will typically comprise a distal port and a guidewire lumen that can extend proximally from the distal port to a proximal port that is disposed proximal to the cutter. In one particular embodiment, the proximal port is disposed approximately 30 cm from the distal port.

The present invention further provides methods of debulking a body lumen. In one method, a catheter is delivered to a target site in the body lumen. A distal portion of the catheter is rotated or deflected relative to a proximal portion of the catheter to expose the tissue debulking device and the body lumen is debulked with the exposed debulking device.

In exemplary embodiments, the methods of the present invention use a cutter to debulk the body lumen. In such embodiments, the cutter is rotated and the cutter is exposed through a cutting window and biased into contact with the material in the body lumen. By coupling the severing and biasing steps, it is easier for the user to control and manipulate the catheter, thus making it easier to perform the atherectomy procedure.

In another method of removing material from a body lumen, a catheter is placed in the body lumen and a distal portion of the catheter is deflected against the body lumen to position a tissue debulking device in a desired position. In some methods the catheter and tissue debulking device can be moved through the material in the body lumen to debulk the body lumen. In exemplary embodiments, a tissue debulking cutter can be rotated and moved from a first, distal position to a second proximal position across a cutting window by retracting a drive shaft through a channel in the catheter. The cutter is exposed or moved out of the cutting window and a distal end of the catheter and cutter are urged against the body lumen. Thereafter, the catheter can be advanced through the body lumen to contact the cutter with the target tissue to debulk the body lumen.

In a still further aspect, kits according to the present invention will comprise a catheter having a rotatable and deflectable cutter. The kits will further include instructions for use setting forth any of the methods described above. Optionally, the kits will further include packaging suitable for containing the catheter and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the catheter will be provided in a sterilized condition. Other kit components, such as a guidewire, may also be included.

For a further understanding of the nature and advantages of the invention, reference should be made to the following description taken in conjunction with the accompanying drawings.

BRIEF DESCRIPTION OF THE DRAWINGS

FIG. 5A is an end view of the distal portion of the debulking catheter of FIG. 5A in which the cutter is in a packing position within a tip of the catheter;

FIG. 5B is a sectional view along Line A-A of FIG. 5A;

FIG. 9A is a perspective view of a cutter of the present invention;

FIG. 9B is an end view of the cutter of FIG. 9A;

FIG. 9C is a sectional view of the cutter along Line A-A of the cutter of FIGS. 9A and 9B;

FIG. 10A is a perspective view of a in-stent restenosis cutter of the present invention;

FIG. 10B is an end view of the cutter of FIG. 10A;

FIG. 10C is a sectional view of the cutter along Line B-B of the cutter of FIGS. 10A and 10B;

DETAILED DESCRIPTION OF THE INVENTION

Figure 1:
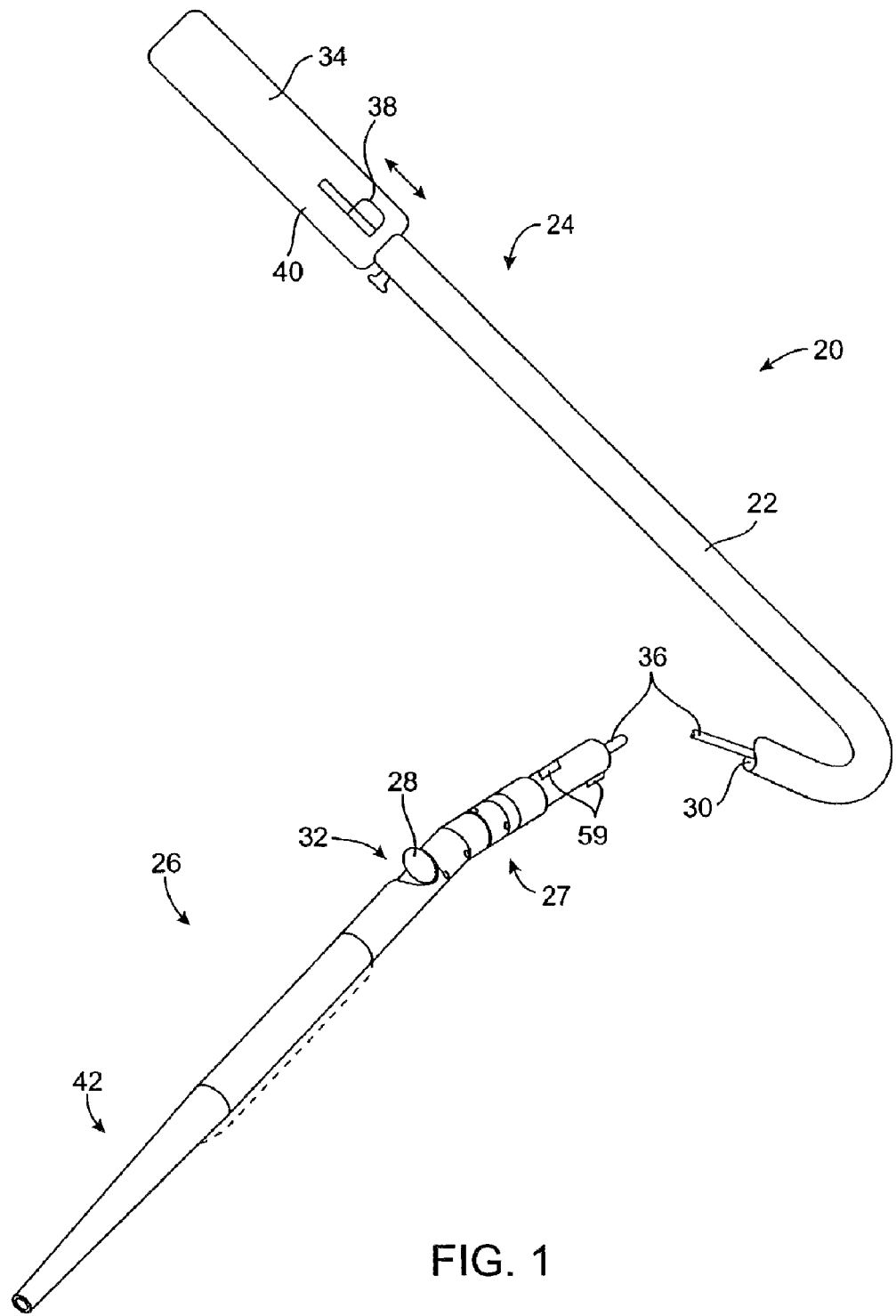
FIG. 1 is a perspective view of a debulking catheter of the present invention.

The methods and systems of the present invention are designed to debulk atheroma and other occlusive material from diseased body lumens, and in particular coronary arteries, de novo lesions, and in-stent restenosis lesions. The systems, devices and methods, however, are also suitable for treating stenoses of the body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Debulking of such material can thus be beneficial to maintain patency of the body lumen. While the remaining discussion is directed at debulking and passing through atheromatous or thrombotic occlusive material in a coronary artery, it will be appreciated that the systems and methods of the present invention can be used to remove and/or pass through a variety of occlusive, stenotic, or hyperplastic material in a variety of body lumens.

Apparatus according to the present invention will generally comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the proximal portions of the catheter bodies will typically be very flexible and suitable for introduction over a guidewire to a target site within the vasculature. In particular, catheters can be intended for "over-the-wire" introduction when a guidewire channel extends fully through the catheter body or for "rapid exchange" introduction where the guidewire channel extends only through a distal tip portion of the catheter body. In other cases, it may be possible to provide a fixed or integral coil tip or guidewire tip on the distal portion of the catheter or even dispense with the guidewire entirely. For convenience of illustration, guidewires will not be shown in all embodiments, but it should be appreciated that they can be incorporated into any of these embodiments.

Catheter bodies intended for intravascular introduction will typically have a length in the range from 50 cm to 200 cm and an outer diameter in the range from 1 French to 12 French (0.33 mm: 1 French), usually from 3 French to 9 French. In the case of coronary catheters, the length is typically in the range from 125 cm to 200 cm, the diameter is preferably below 8 French, more preferably below 7 French, and most preferably in the range from 2 French to 7 French. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, coils, axial filaments, or the like, in order to increase rotational strength, column strength, toughness, pushability, and the like. Suitable catheter bodies may be formed by extrusion, with one or more channels being provided when desired. The catheter diameter can be modified by heat expansion and shrinkage using conventional techniques. The resulting catheters will thus be suitable for introduction to the vascular system, often the coronary arteries, by conventional techniques.

The distal portion of the catheters of the present invention may have a wide variety of forms and structures. One aspect of the present invention provides catheters having a reduced rigid length. The reduced rigid lengths can allow the catheters to access and treat tortuous vessels and small diameter body lumens. In most embodiments a rigid distal portion or housing of the catheter body will have a diameter that generally matches the proximal portion of the catheter body, however, in other embodiments, the distal portion may be larger or smaller than the flexible portion of the catheter.

The rigid distal portion of the catheter body can be formed from materials which are rigid or which have very low flexibilities, such as metals, hard plastics, composite materials, NiTi, steel with a coating such as titanium, tantalum nitride, ME-92®, diamonds, or the like. Most usually, distal end of the catheter body will be formed from stainless steel or platinum/iridium. The length of the rigid distal portion may vary widely, typically being in the range from 5 mm to 35 mm, more usually from 10 mm to 25 mm, and preferably between 6 mm and 8 mm. In contrast, conventional catheters typically have rigid lengths of approximately 16 mm.

The side opening windows of the present invention will typically have a length of approximately 2 mm. In other embodiments, however, the side opening cutting window can be larger or smaller, but should be large enough to allow the cutter to protrude a predetermined distance that is sufficient to debulk material from the body lumen.

The catheters of the present invention can include a flexible atraumatic distal tip coupled to the rigid distal portion of the catheter. For example, an integrated distal tip can increase the safety of the catheter by eliminating the joint between the distal tip and the catheter body. The integral tip can provide a smoother inner diameter for ease of tissue movement into a collection chamber in the tip. During manufacturing, the transition from the housing to the flexible distal tip can be finished with a polymer laminate over the material housing. No weld, crimp, or screw joint is usually required.

The atraumatic distal tip permits advancing the catheter distally through the blood vessel or other body lumen while reducing any damage caused to the body lumen by the catheter. Typically, the distal tip will have a guidewire channel to permit the catheter to be guided to the target lesion over a guidewire. In some exemplary configurations, the atraumatic distal tip comprises a coil. In some configurations the distal tip has a rounded, blunt distal end. The catheter body can be tubular and have a forward-facing circular aperture which communicates with the atraumatic tip. A collection chamber can be housed within the distal tip to store material removed from the body lumen. The combination of the rigid distal end and the flexible distal tip is approximately 30 mm.

A rotatable cutter or other tissue debulking assembly may be disposed in the distal portion of the catheter to sever material which is adjacent to or received within the cutting window. In an exemplary embodiment, the cutter is movably disposed in the distal portion of the catheter body and movable across a side opening window. A straight or serrated cutting blade or other element can be formed integrally along a distal or proximal edge of the cutting window to assist in severing material from the body lumen. In one particular embodiment, the cutter has a diameter of approximately 1.14 mm. It should be appreciated however, that the diameter of the cutter will depend primarily on the diameter of the distal portion of the catheter body.

In exemplary embodiments, activation of an input device can deflect a distal portion of the catheter relative to the proximal portion of the catheter so as to expose a debulking assembly. In some embodiments, activation of the input device moves the debulking assembly over a ramp or cam so that a portion of the rigid distal portion and flexible tip are caused to drop out of the path of the debulking assembly so as to expose the debulking assembly through the window. Deflection of the distal housing increases the effective "diameter" of the catheter and causes the debulking assembly to be urged adjacent to the lumen wall and target tissue.

In exemplary embodiments, the debulking assembly comprises a rotatable cutter that is movable outside the window. By moving the cutter outside of the cutting window beyond an outer diameter of the distal portion of the catheter, the cutter is able to contact and sever material that does not invaginate the cutting window. In a specific configuration, the rotating cutter can be moved over the cam within the rigid portion of the catheter body so that the cutting edge is moved out of the window. Moving the rotating cutter outside of the cutting window and advancing the entire catheter body distally, a large amount of occlusive material can be removed. Consequently, the amount of material that can be removed is not limited by the size of the cutting window. As will be described in detail below, in some situations it is preferable to provide a serrated cutting edge, while in other situations it may be preferable to provide a smooth cutting edge. Optionally, the cutting edge of either or both the blades may be hardened, e.g., by application of a coating. A preferred coating material is a chromium based material, available from ME-92, Inc., which may be applied according to manufacturer's instructions. Other rotatable and axially movable cutting blades are described in U.S. Pat. Nos. 5,674,232; 5,242,460; 5,312,425; 5,431,673; and 4,771,774, the full disclosures of which are incorporated herein by reference.

The catheters of the present invention may include a monorail delivery system to assist in positioning the cutter at the target site. For example, the tip of the catheter can include lumen(s) that are sized to receive a conventional guidewire (typically 0.014' diameter) and the flexible proximal portion of the catheter body can include a short lumen (e.g., about 12 centimeters in length). Such a configuration moves the guidewire out of the rigid portion so as to not interfere with the debulking assembly.

In other embodiments, however, if desired the guidewire lumen may be disposed within or outside the flexible proximal portion of the catheter body and run a longer or shorter length, and in fact may run the entire length of the flexible portion of the catheter body. The guidewire can be disposed within lumen on the flexible portion of the catheter body and exit the lumen at a point proximal to the rigid portion of the catheter. The guidewire can then enter a proximal opening in the tip lumen and exit a distal opening in the tip lumen.

The present invention may optionally employ any of a wide variety of conventional radiopaque markers, imaging devices, and/or transducers. In exemplary embodiments, the catheters of the present invention can include a radiopaque distal portion and/or radiopaque markers disposed on a distal portion of the catheter body, such as proximal and distal of the cutting window, on the cam or ramp, so as to allow the user to track the position of the cutter, or the like. The catheters of the present invention will also be particularly useful with ultrasonic transducers, such as an IVUS, of a type which may be deployed linearly within the catheter body or circumferentially on the debulking assembly. Linear deployment will allow viewing along a discrete length of the catheter axis, preferably adjacent to the cutting point, usually over a length in the range from 1 mm to 30 mm, preferably 2 mm to 10 mm. Circumferentially deployed phased arrays may subtend a viewing arc in the range from 5° to 360°, usually from 180° to 360°. For imaging transducers located on cutting blades within a housing or second cutting element, the field of imaging will generally be limited by the dimensions of the aperture. In some cases, however, it might be possible to fabricate all or a portion of the cutter blade/housing out of an ultrasonically translucent material. A more complete description of suitable imaging catheters are described more fully in U.S. patent application Ser. No. 09/378,224, filed Aug. 19, 1999, and entitled "Atherectomy Catheter with Aligned Imager," now U.S. Pat. No. 6,299,622 B1, the complete disclosure of which is incorporated herein by reference. In addition to ultrasonic array transducers, the imaging devices of the present invention may comprise optical coherence tomography devices, such as described in U.S. Pat. No. 5,491,524, the full disclosure of which is incorporated herein by reference, as well as Huang et al. (1991) Science 254:1178-1181; Brezinski et al. (1997) Heart 77:397-403; and Brezinski et al (1996) Circulation 93:1206-1213. In some instances, the present invention may also provide optical imaging using optical wave guides and the like.

Referring now to FIG. 1, a catheter 20 constructed in accordance with principles of the present invention comprises a catheter body 22 having a proximal portion 24 and a distal portion 26. Proximal portion 24 can be coupled to distal portion 26 with a connection assembly 27 to allow pivoting or deflection of distal portion 26 relative to proximal portion 24. A proximal end of the catheter body 22 can have a handle 40 for manipulation by a user, a luer for connection to an aspiration of fluid delivery channel, or the like.

A debulking assembly 28, such as a cutter, is disposed within a lumen 30 of the catheter body 22. The cutter is typically rotatable within distal portion about an axis that is parallel to the longitudinal axis of the rigid portion 26 of catheter and axially movable along the longitudinal axis. The cutter 28 can access target tissue through a side opening window 32 which is typically large enough to allow the cutter 28 to protrude through and move out of the window a predetermined distance. The cutter is coupled to a cutter driver 34 through a coiled drive shaft 36. Actuation of a movable actuator or other input device 38 can activate the drive shaft 36 and cutter, move cutter 28 longitudinally over a cam so as to deflect the distal portion and move the cutter 28 out of cutting window 32. Camming of the cutter 28 can cause the distal rigid portion 26 to pivot or deflect relative to the proximal portion 24 so as to deflect and urge the cutter into the tissue in the body lumen.

In some embodiments, the distal portion 26 of the catheter will be moved to an angled or offset configuration from the longitudinal axis of the proximal portion 24 of the catheter and the cutter 28. In some embodiments, the cutter 28 can also be deflected off of the axis of the proximal and/or distal portion of the catheter.

The catheters 20 of the present invention typically have a flexible proximal portion 24, a rigid distal portion 26, and a flexible distal tip 42. The flexible proximal portion 24 of the catheter is typically a torque shaft and the distal portion is typically a rigid tubing. The torque shaft 24 facilitates transportation of the catheter body 22 and cutter 28 to the diseased site. The proximal end of the torque shaft 24 is coupled to a proximal handle 40 and the distal end of the torque shaft is attached to the distal, rigid portion 26 of the catheter through the connection assembly 27. The drive shaft 36 is movably positioned within the torque shaft 24 so as to rotate and axially move within the torque shaft 24. The drive shaft 36 and torque shaft 24 are sized to allow relative movement of each shaft without interfering with the movement of the other shaft. The catheter body will have the pushability and torqueability such that torquing and pushing of the proximal end will translate motion to the distal portion 26 of the catheter body 22.

Figure 2:
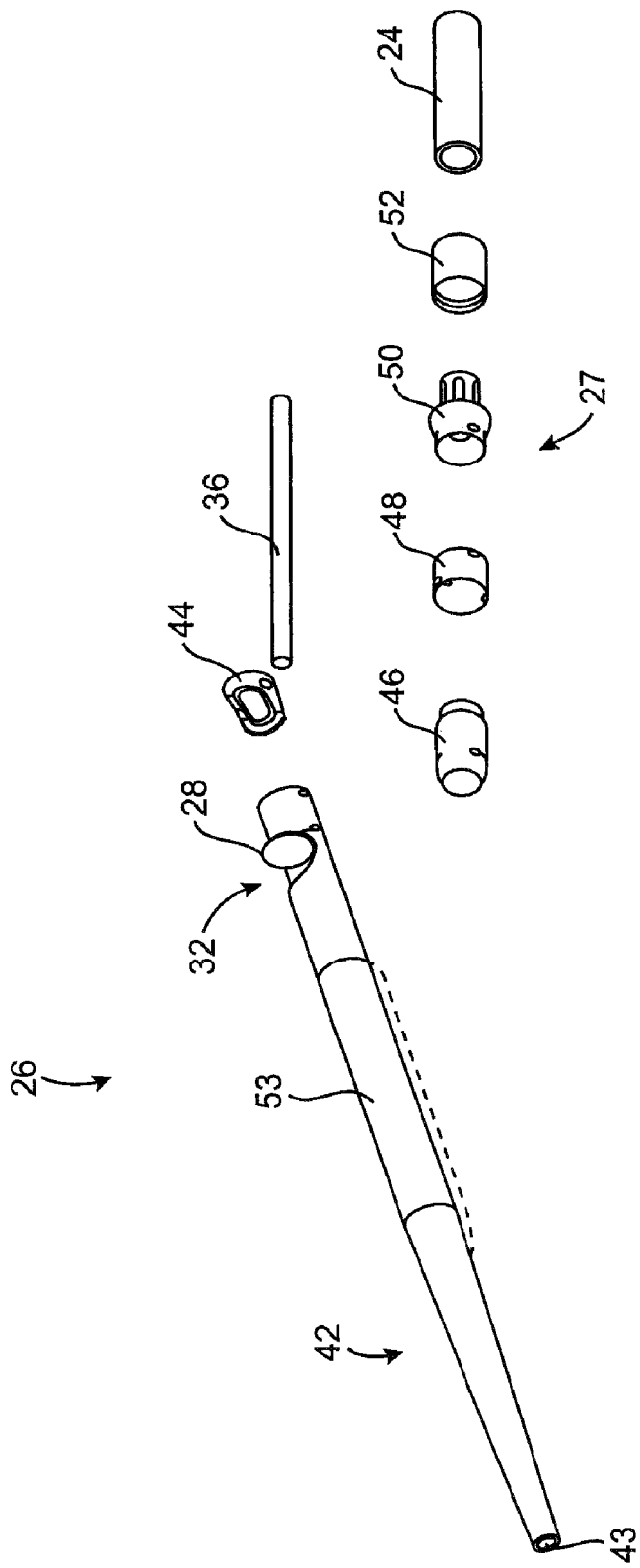
FIG. 2 is an exploded view of an exemplary distal portion of the debulking catheter of the present invention.

FIG. 2 illustrates an exploded view of a distal end of the catheter. In such embodiments, the catheter 10 includes a connection assembly 27, a rigid housing 26, a distal tip 42 that at least partially defines a collection chamber 53 for storing the severed atheromatous material, and a lumen that can receive the guidewire. The distal tip 42 can have a distal opening 43 that is sized to allow an imaging guidewire or conventional guidewire (not shown) to be advanced distally through the tip.

A ramp or cam 44 can at least partially fit within the lumen in the distal housing. As will be described in detail below, proximal movement of the cutter 28 over the ramp 44, causes the deflection of the distal housing 26 and guides cutter 28 out of cutting window 32. Attached to the ramp 44 is a housing adaptor 46 that can connect one or more articulation member 48 to the distal tip to create an axis of rotation of the distal portion 26. The housing adaptor 46 and articulation member 48 allow the distal end of the catheter to pivot and bias against the body lumen. In the illustrated embodiment there are only housing adaptor 46 and one articulation member 48, but it should be appreciated that the catheters of the present invention can include, two, three, or more joints (e.g., axis of rotation), if desired. Moreover, the axes of rotation can be parallel or non-parallel with each other.

The catheter can also include a shaft adaptor 50 and collar 52 to couple articulation member 48 to the torque shaft 22. Shaft adaptor 50 can connect the housing to the torque shaft and collar 52 can be placed over a proximal end of the shaft adaptor and crimped for a secure attachment. It should be appreciated by one of ordinary skill in the art that that while one exemplary catheter of the present invention has the above components that other catheters of the present invention may not include more or less of the components described above. For example, some components can be made integral with other components and some components may be left out entirely. Thus, instead of having a separate ramp 44, the ramp may be integrated with the distal tip to direct the cutter out of the cutting window.

As shown in FIGS. 3A to 5B, the cutters 28 of the present invention will generally be movable between two or more positions. During advancement through the body lumen, the cutter will generally be in a neutral position (FIGS. 3A and 3B) in which the cutter is distal of cutting window 32. In some embodiments, an imaging device (not shown) can be coupled to cutter 28 so as to image the body lumen through cutting window 32 when cutter 28 is in the neutral position. Once the catheter has reached the target site, the cutter can be moved to an open position (FIGS. 4A and 4B) in which the cutter is moved to a proximal end of the cutting window and will extend out of the cutting window a distance L beyond an outer diameter D of the rigid portion 26. In most embodiments, in the open position, the cutter will have deflected the distal portion and the cutter's axis of rotation will generally be in line with connection assembly 27 but angled or offset from longitudinal axis of the distal portion of the catheter body.

Optionally, in some embodiments, cutter 28 can be moved to a packing position, in which the cutter is moved distally, past the neutral position, so as to pack the severed tissue into a distal collection chamber 53 (FIGS. 5A and 5B). It should be appreciated however, that while the exemplary embodiment moves the cutter to the above described positions, in other embodiments of the present invention the cutter can be positioned in other relative positions. For example, instead of having the neutral position distal of the cutting window, the neutral position may be proximal of the window, and the open position may be along the distal end of the cutting window, or the like.

Figure 4A:
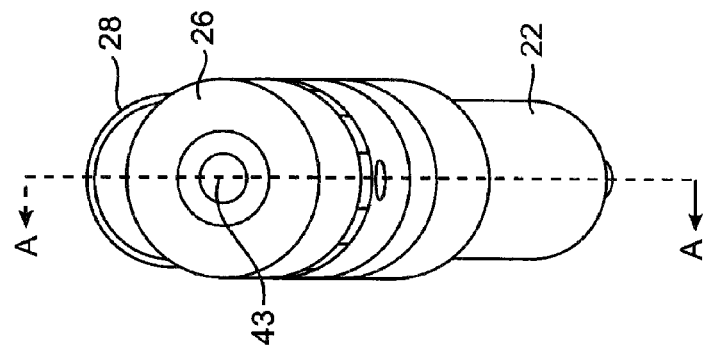
FIG. 4A is an end view of the distal portion of the debulking catheter of FIG. 4A in which the cutter is in an open position outside of the cutting window.
Figure 4B:
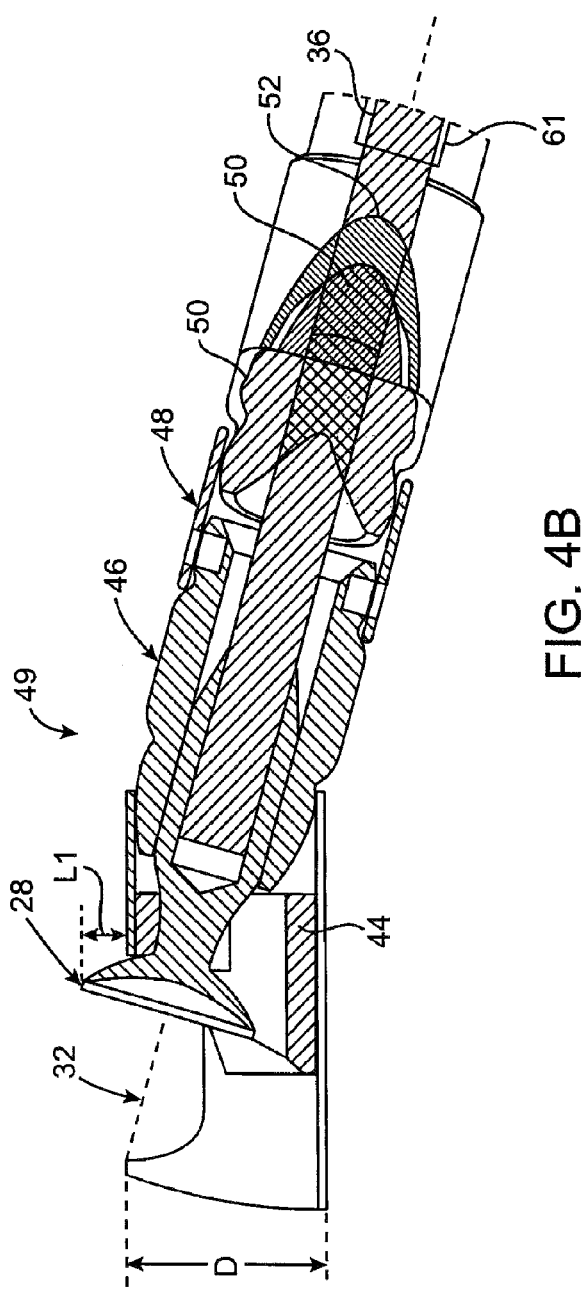
FIG. 4B is a sectional view along Line A-A of FIG. 4A.

Referring again to FIGS. 4A and 4B, the interaction of the components of the rigid distal portions 26 in one exemplary embodiment of the present invention will be further described. As shown in FIG. 4B, the cutting window 32 is typically a cutout opening in the distal portion 26. While the size of the cutting window 32 can vary, the cutting window should be long enough to collect tissue and circumferentially wide enough to allow the cutter to move out of the cutting window during cutting, but sized and shaped to not expel emboli into the vasculature.

Cams or ramp 44 (shown most clearly in FIG. 4B) can be disposed in the distal portion of the catheter body to guide or otherwise pivot the cutter 28 out of the cutting window 32 as the cutter 28 pulled proximally through tensioning of drive shaft 36.

A joint is located proximal to the cutting window 32 to provide a pivot point for camming of the distal portion 26 relative to the proximal portion 24. The bending at a flexible joint 49 is caused by the interaction of cams or ramps 44 with cutter 28 and the tensile force provided through drive shaft 36. In the exemplary configuration, the joint includes a housing adaptor 46 that is pivotally coupled to the distal rigid portion 26. As shown in FIGS. 4A and 4B, the resulting pivoting of the rigid distal portion 26 relative to the proximal portion causes a camming effect which urges the distal housing against the body lumen wall without the use of urging means (e.g., a balloon) that is positioned opposite of the cutting window. Thus, the overall cross sectional size of the catheter bodies can be reduced to allow the catheter to access lesions in smaller body lumens. In exemplary embodiments, the distal housing can deflect off of the axis of the proximal portion of the catheter typically between 0° degrees and 30° degrees, usually between 5° degrees and 20° degrees, and most preferably between 5° degrees and 10° degrees. The angle of deflection relates directly to the urge. Urge however, not necessarily relate to force but more to the overall profile of the catheter. For example, the greater the angle of deflection, the larger the profile and the bigger the lumen that can be treated. The ranges were chosen to allow treatment of vessels ranging from less than 2 mm to greater than 3 mm within the limits of mechanical design of the components. It should be appreciated however, that the angles of deflection will vary depending on the size of the body lumen being treated, the size of the catheter, and the like.

The deflection of the distal portion 26 of the catheter urges the cutter into position such that distal advancement of the entire catheter body can move the rotating cutter through the occlusive material. Because the cutter is moved a distance $L_1$ beyond the outer diameter of the distal portion of the catheter and outside of the cutting window, the user does not have to invaginate the tissue into the cutting window. In exemplary configurations, the cutter can typically be moved between approximately 0.08 mm and 0.64 mm, preferably between 0.25 mm and 0.50 mm, and most preferably between 0.28 to 0.38 mm beyond the outer diameter of the distal housing to contact the material within the body lumen. It should be appreciated that the cutter excursion directly relates to the depth of cut. The higher the cutter moves out of the cutting window the deeper the cut. The ranges are chosen around efficacy without risk of perforation of the body lumen.

Figure 3A:
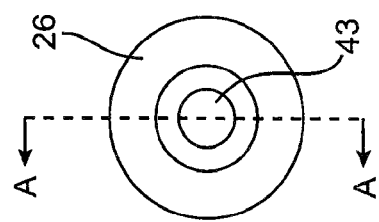
FIG. 3A is an end view of the distal portion of the debulking catheter of FIG. 3A in which the cutter is in a closed position in the catheter body.
Figure 3B:
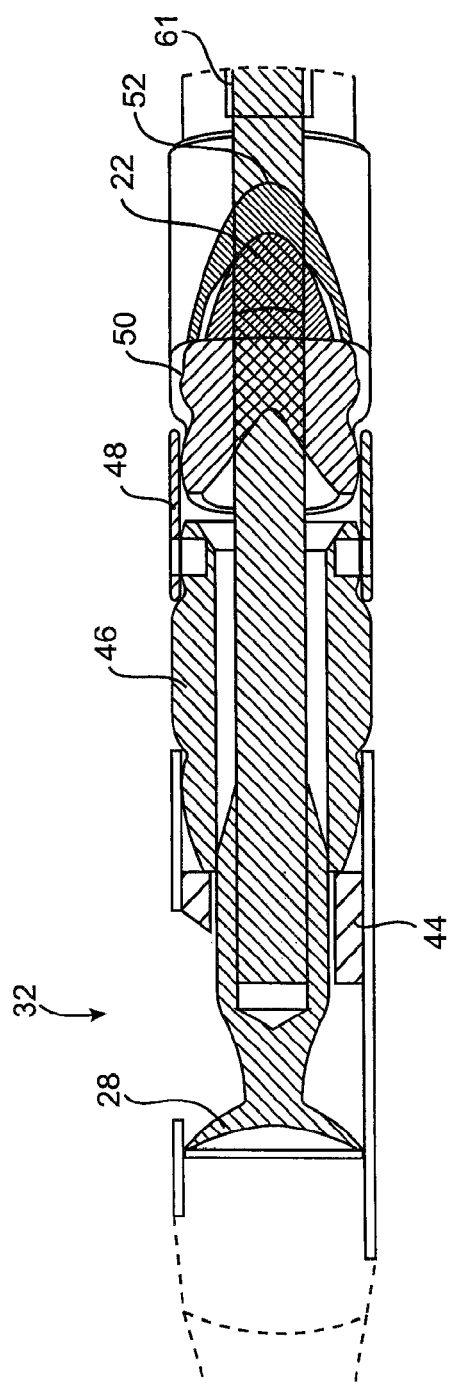
FIG. 3B is a sectional view along Line A-A of FIG. 3A.

Pushing the entire catheter across the lesion removes the tissue from the body lumen. The severed tissue is collected as the severed piece is directed into a collection chamber 53 in the tip via the cutter 28. Once the catheter and cutter 28 have moved through the lesion, the cutter 28 can be advanced distally to a "part off position" in which the cutter is moved back into the cutting window 32 (FIG. 3B). The tissue is collected as the severed pieces of tissue are directed into a collection chamber 53 via the distal movement of cutter 28 and catheter. The collection chamber 53 of the tip and distal portion 26 acts as a receptacle for the severed material to prevent the severed occlusive material from entering the body lumen, and possibly causing downstream occlusions. The cutter 28 can interact with the distal edge of the cutting window to part off the tissue and thereafter pack the severed tissue into collection chamber 53 (FIG. 3B). In exemplary embodiments, the driver motor can be programmed to stop the rotation of the cutter at the part off position so that cutter move to a third position (FIG. 5B) and can pack the material in the collection chamber in the tip without rotation. Typically, the collection chamber 53 will be large enough to allow multiple cuts to be collected before the device has to be removed from the body lumen. When the collection chamber is full, or at the user's discretion, the device can be removed, emptied and reinserted over the guidewire via a monorail system, as will be described below.

Figure 6:
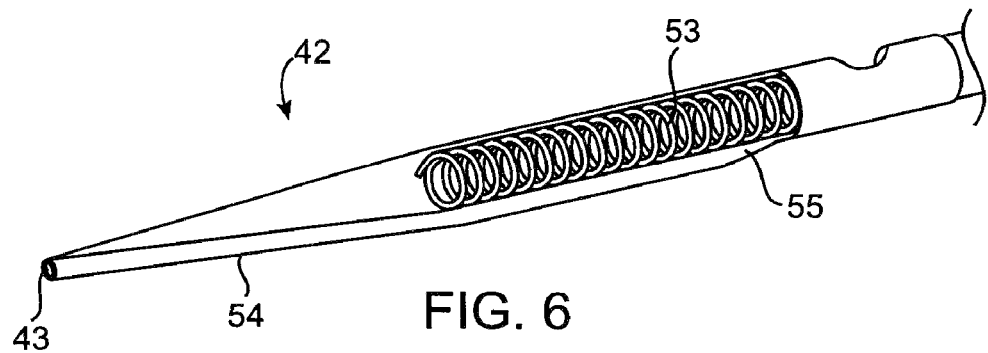
FIGS. 6 to 8 illustrate a monorail delivery system of the present invention.
Figure 7:
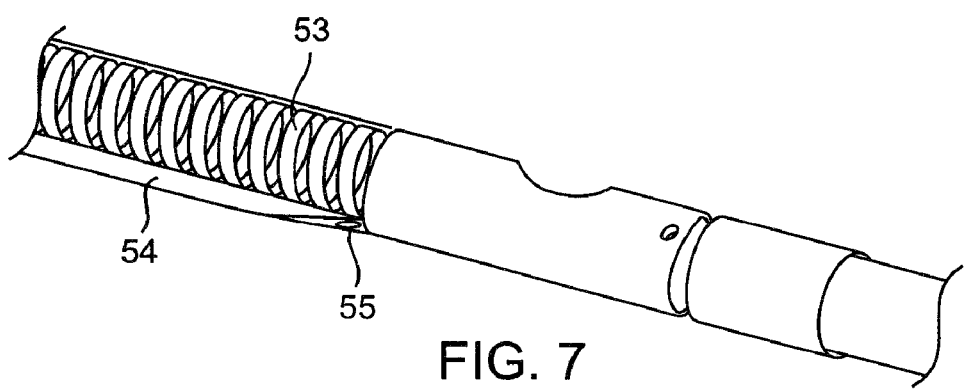
Figure 8:
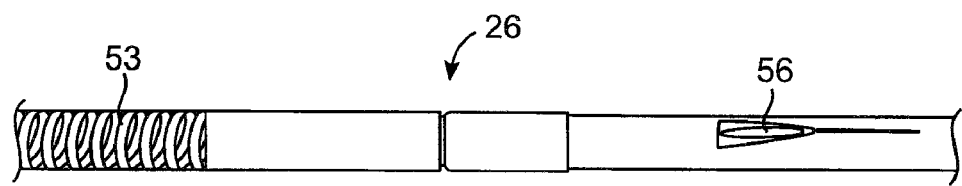
Figure 11A:
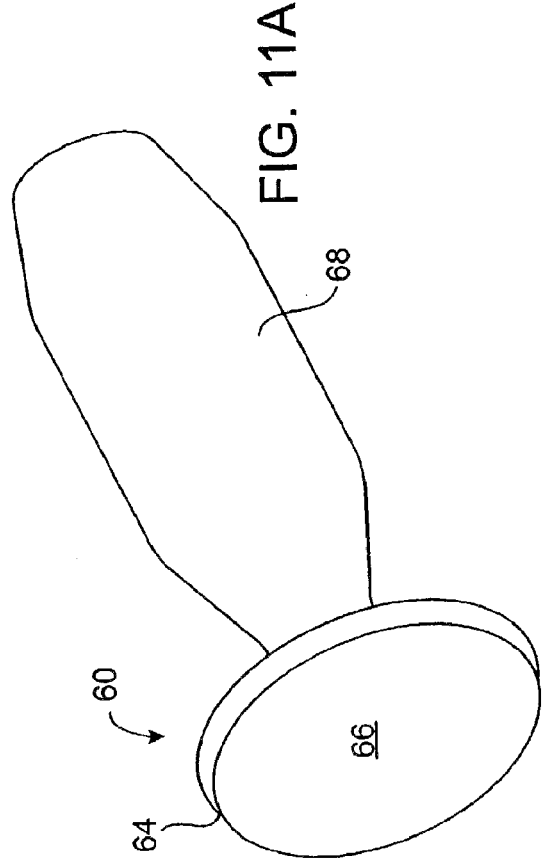
FIG. 11A is a perspective view of another in-stent restenosis cutter of the present invention.
Figure 11C:
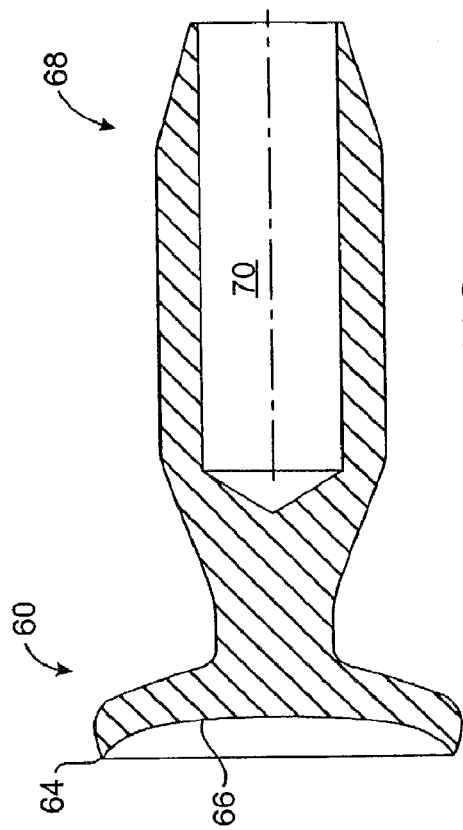
FIG. 11C is a sectional view of the cutter along Line C-C of the cutter of FIGS. 11A and 11B.
Figure 11B:
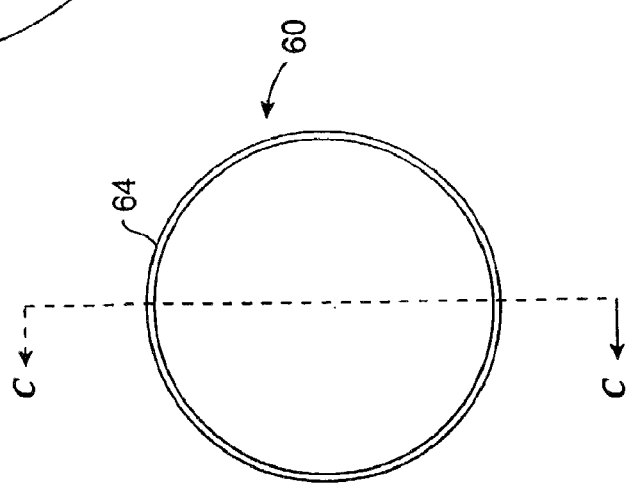
FIG. 11B is an end view of the cutter of FIG. 11A.

FIGS. 6 to 8 illustrate one exemplary monorail delivery system to assist in positioning the cutter 28 at the target site. For example, tip 42 of the catheter can include a lumen 54 having a distal opening 43 and a proximal opening 55 that is sized to receive a conventional guidewire (typically 0.014" diameter) and as shown in FIG. 8, the flexible proximal portion of the catheter body can include a short lumen 56 (e.g., about 12 centimeters in length). In some embodiments, however, the guidewire lumen 56 may be disposed within or outside the flexible proximal portion of the catheter body and run a longer or shorter length, and in fact may run the entire length of the flexible portion 24 of the catheter body. In use, the guidewire can be disposed within lumen 56 on the flexible portion of the catheter body and exit the lumen at a point proximal to the rigid portion 26 of the catheter. The guidewire can then re-enter a proximal opening 55 in the tip lumen 54 and exit through distal opening 43 in the tip lumen. By moving the guidewire outside of the rigid portion 26 of the catheter body, the guidewire will be prevented from tangling with the cutter 28. Typically, tip lumen 54 will be disposed along a bottom surface of the tip and the lumen 56 will be disposed along a side of the proximal portion 22 of the catheter body so that the guidewire will be in a helical configuration.

The catheters of the present invention can include radiopaque markers so as to allow the user to track the position of the catheter under fluoroscopy. The rigid distal portion 26 can be radiopaque and radiopaque markers can be disposed on the flexible shaft. Typically, the markers 59 will be disposed along the top, proximal to the cutting window, and on the bottom of the catheter to let the user know the position of the cutter and cutting window relative to the target site. If desired, the top and bottom markers can be different shaped so as to inform the user the relative orientation of the catheter in the body lumen. Because the guidewire will form a helix in its transition from lumen 56 to tip lumen 54, the user will be able to view the top and bottom radiopaque markers 59 without interference from the guidewire. Some embodiments of the catheter can also include a radiopaque cutter stop 61 (FIG. 3B) that is crimped to driveshaft 36 proximal of the cutter that moves with the cutter so as to let the user know when the cutter is in the open position.

FIGS. 9A to 11C show some exemplary embodiments of the cutter 28 of the present invention. The distal portion 60 of the rotatable cutter 28 can include a serrated knife edge 62 or a smooth knife edge 64 and a curved or scooped distal surface 66. A proximal portion 68 of the cutter 28 can include a channel 70 that can be coupled to the drive shaft 36 that rotates the cutter. As shown in FIGS. 10A-10C, some embodiments of the cutters can include a bulge or bump 69 that is provided to interact with a stent so as to reduce the interaction of the cutting edge with the stent.

Figure 12:
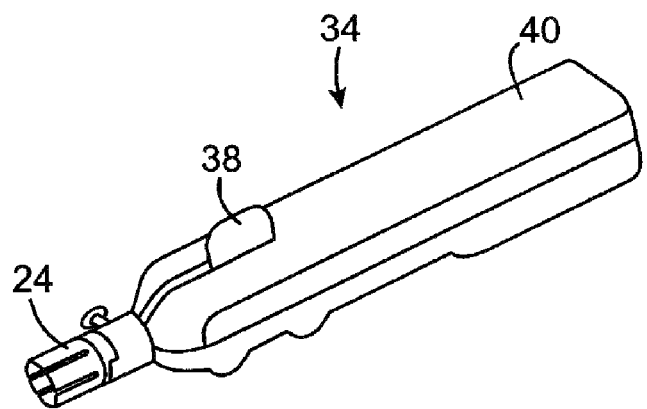
FIG. 12 illustrates a proximal handle and cutter driver of the present invention.
Figure 13:
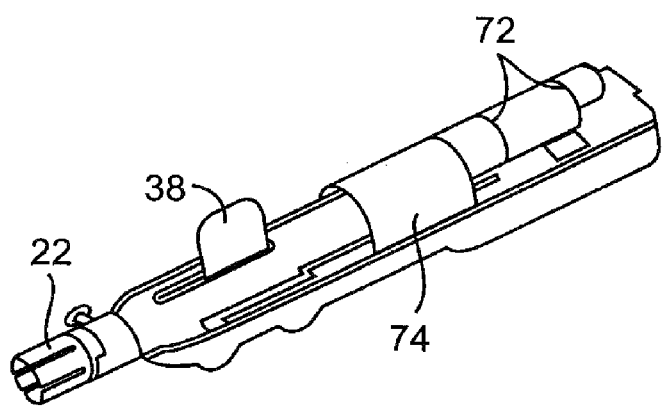
FIG. 13 illustrates a cutter driver with a handle cover removed.
Figure 14:
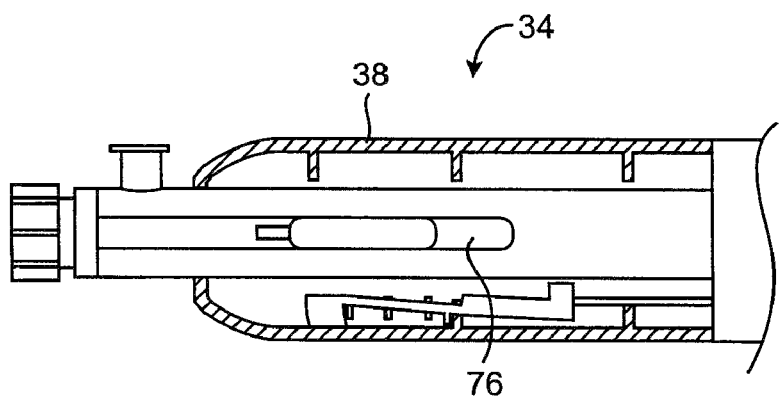
FIGS. 14 to 16 illustrate three positions of the lever for controlling the cutter.

FIGS. 12 to 16 illustrate an exemplary cutter driver 34 of the present invention. As shown in FIGS. 12 and 13, cutter driver 34 can act as the handle for the user to manipulate the catheters 20 of the present invention as well as a power source. Typically, the cutter drivers 34 of the present invention include a single input device, such as a lever 38 that controls the major operations of the catheter (e.g., axial movement to cause urging, rotation to cause cutting, and axial movement for packing). As shown in FIGS. 13 and 14, cutter driver 34 includes a power source 72 (e.g., batteries), a motor 74, a microswitch 76 for activating motor 74, and a connection assembly (not shown) for connecting the drive shaft 36 to the driver motor 74. In some embodiments, the drive motor can rotate drive shaft 36 between 1,000 rpm and 10,000 rpm or more, if desired.

Figure 15:
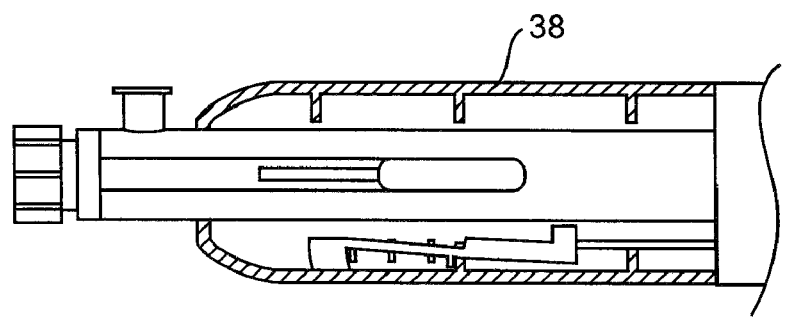
Figure 16:
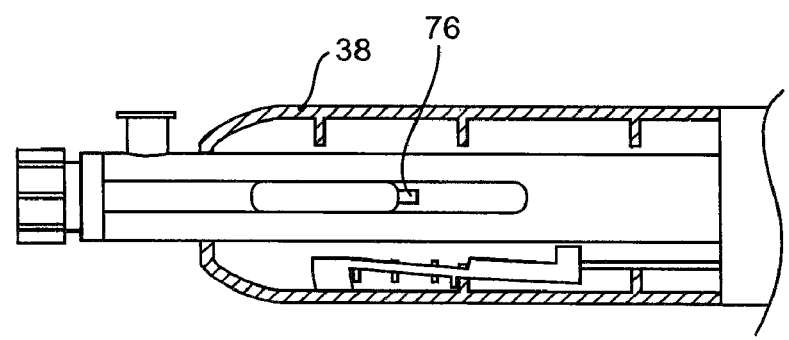

FIGS. 14 to 16 illustrate one exemplary method of operating cutter driver 34. In use, the catheter will be delivered to the target site with cutter driver unattached and the cutter in the neutral position (FIG. 3B). The cutter driver can be attached with the urge lever 38 in a neutral position (FIG. 14), which indicates that the cutter is closed, but not in a packing position. The user can then move the catheter (and cutter driver unit, if desired) to position the distal portion 26 of the catheter adjacent the target tissue. As shown in FIG. 15, to activate the rotation of the cutter, the urge lever 38 can be moved proximally from the neutral position to move the cutter proximally and out of cutting window 32 (FIG. 4B) and simultaneously depressing microswitch 76 to activate motor 74. At the end of the cutting procedure, as shown in FIG. 16, the user can push urge lever 38 completely forward to a distal position to push the cutter into a packing position (FIG. 5B). After the urge lever passes the middle of the travel, the microswitch 76 can be released so as to deactivate the cutter before reaching the packing position such that packing can occur without the cutter rotating. It should be appreciated, while the figures illustrate the use of an urge lever or thumb switch as an input device, the present invention can use other type of input devices, such as labeled buttons (e.g., close window, debulk tissue, and pack), or the like.

Advantageously, cutter driver 34 provides an automatic on/off control of the cutter 28 that is keyed to the position of the cutter. Such a configuration frees the user from the complicated task of remembering the sequence of operations to activate and deactivate the rotation and axial movement of the cutter.

While the cutter driver 34 is illustrated as a disposable battery powered unit, it should be appreciated that in other embodiments, the cutter driver can use other power sources to control the cutter driver. It should further be appreciated that other cutter drivers can be used with the present invention. While not preferred, it is possible to have separate controls to control the axial movement of the cutter and the rotation of the cutter.

Figure 17:
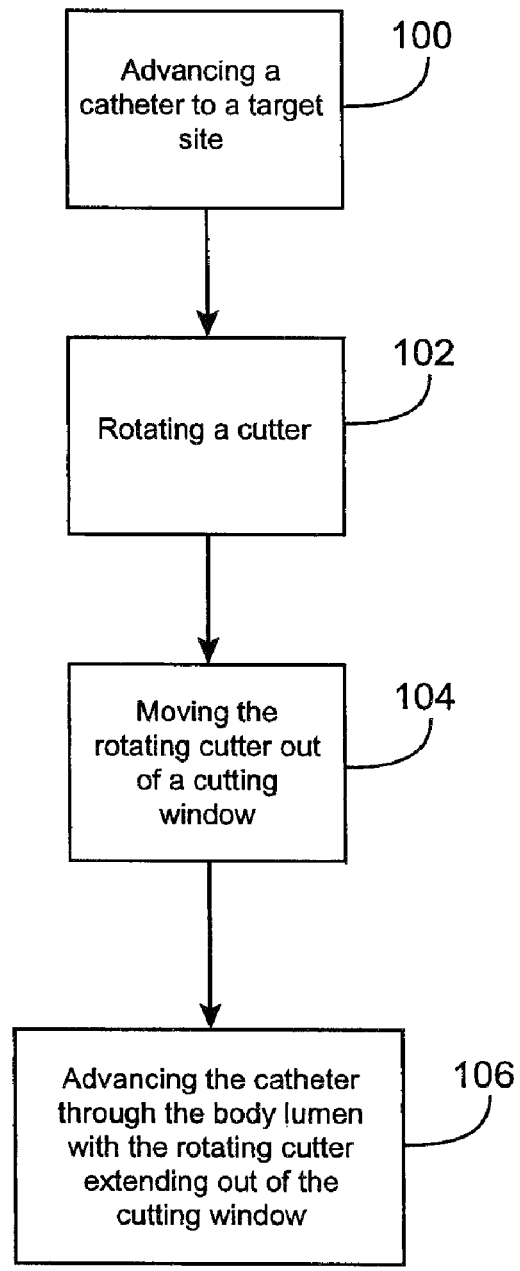
FIG. 17 is a simplified flow chart illustrating a method of the present invention.

Some exemplary methods of the present invention will now be described. One method of the present invention comprises delivering a catheter to a target site in the body lumen. A distal portion of the catheter can be deflected relative to a proximal portion of the catheter to expose a tissue debulking device in the catheter. The body lumen can be debulked with the exposed debulking device. Specifically, as shown schematically in FIG. 17, one specific method comprises advancing a catheter to a target site (Step 100). A cutter can be rotated and moved out of the cutting window (Steps 102, 104). Preferably, a distal portion of the catheter can be pivoted or deflected so as to position the cutter adjacent the target material. Thereafter, the catheter and the rotating cutter can be moved through the body lumen to remove the target material from the body lumen (Step 106).

Figure 18:
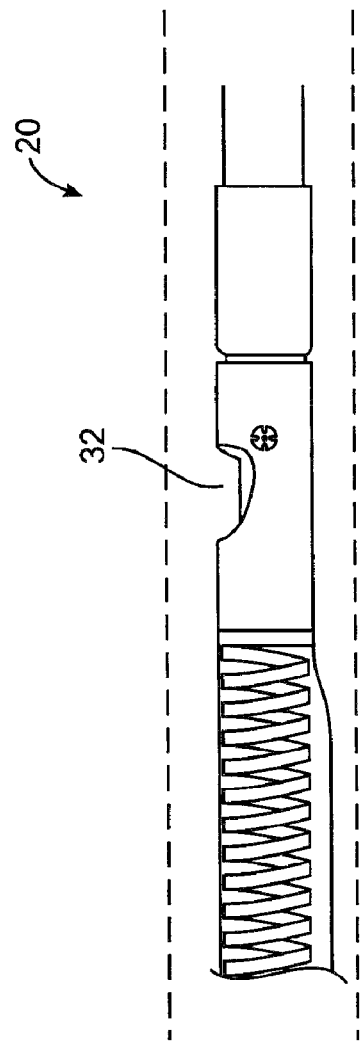
FIGS. 18 and 19 illustrate a method of the present invention.
Figure 19:
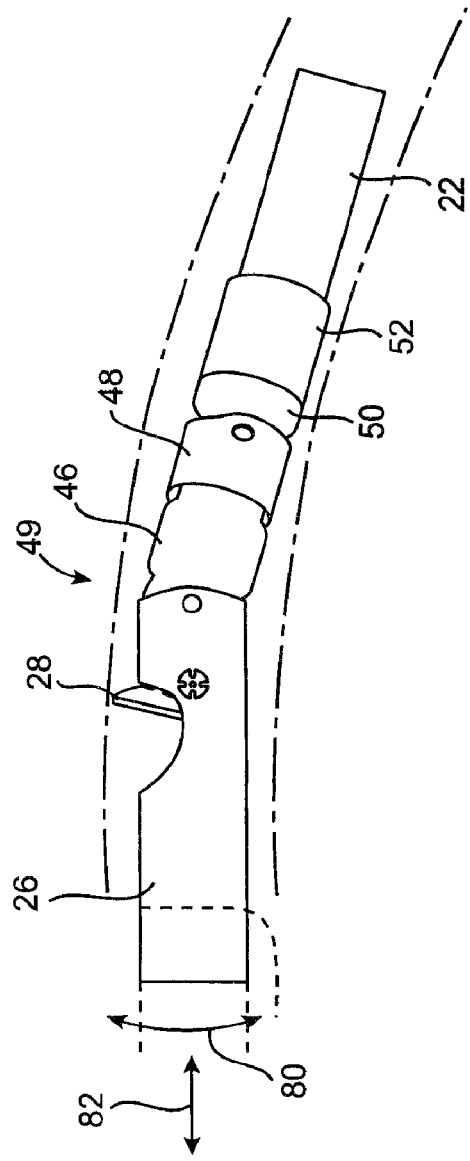

As shown in FIGS. 18 and 19, the catheter can be percutaneously advanced through a guide catheter or sheath and over a conventional or imaging guidewire using conventional interventional techniques. The debulking catheter 20 can be advanced over the guidewire and out of the guide catheter to the diseased area. As shown in FIG. 18, the window 32 will typically be closed (with the cutter or other debulking device 28 in a first, distal position). As shown in FIG. 19, catheter 20 will typically have at least one hinge or pivot connection to allow pivoting about one or more axes of rotation to enhance the delivery of the catheter into the tortuous anatomy without dislodging the guide catheter or other sheath. The cutter can be positioned proximal of the lesion. Optionally, a transducer, IVUS, or other imaging assembly can be used to verify the position of the debulking catheter.

Once the position of the catheter is confirmed, the cutter 28 will be retracted proximally and moved out of cutting window 32 to its second, exposed position. In some embodiments, movement of the cutter can deflect the distal portion of the catheter to increase the profile of the catheter at the target site. Movement of the cutter is typically caused by proximal movement of lever 38 and tensioning of drive shaft 36. Movement of the lever can be scaled to any desired ratio or a direct 1:1 ratio of movement between the handle and cutter. When the cutter is moved proximally it contacts ramp or cam surfaces so as to guide the cutter up and at least partially out of the cutting window 32. Additionally, as shown by arrow 80, the distal portion of catheter body 26 rotates about the joint 49 to provide an urging force for the cutter (and catheter body) to move toward the diseased area.

Thereafter, as shown by arrow 82 the operator can move the entire catheter body 22 through the lesion to dissect the tissue. As the cutter 28 and catheter body 22 are advanced distally through the lesion, tissue that is trapped between the cutting edge 52 and the cutting window 32 is severed from the body lumen. To part off the tissue, the operator can stop pushing the device distally and the cutter can be advanced distally inside the cutting window by advancing the handle 38. During the distal movement of the cutter, the cutter 28 rides back over the ramps 44 and direct the cutter back inside of the cutting window 32. Such movement causes the distal portion 26 of the catheter to move in line with the cutter and proximal portion 24 (FIG. 5B). When the cutter has moved to its distal position, the cutter parts off the severed tissue and urges the severed tissue inside of a collection chamber 53 in the distal tip 42. Optionally, after the cutter 28 has parted off the tissue, the lever 38 and thus the non-rotating cutter 38 can be advanced distally to pack the tissue into the collection chamber 53 (FIG. 5B). Use of the cutter to pack the severed tissue will allow the operator multiple specimens to be collected prior to removing the catheter 20 from the body lumen. When it is determined that the collection chamber is full, the catheter can be removed from the body lumen and the collection chamber can be emptied.

Figure 20:
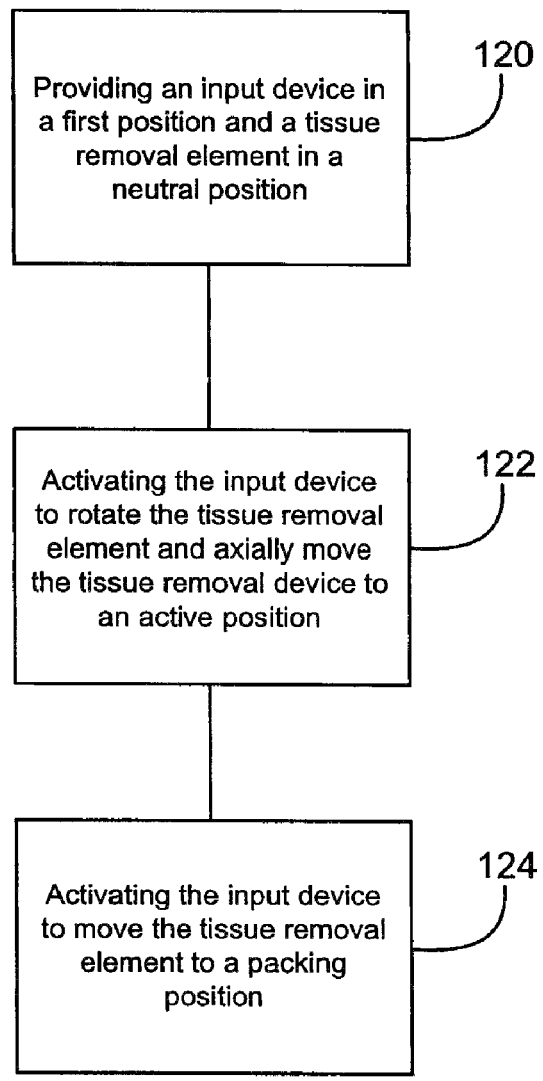
FIG. 20 schematically illustrates another method of the present invention.

In another method of the present invention, as shown in FIG. 20, an input device is disposed in a first position to position a tissue removal element in a neutral position (Step 120). The input device is activated to rotate the tissue removal element and to axially move the tissue removal device to an active position (Step 122). The input device can then be activated again to move the tissue removal element to a packing position (Step 124). In an exemplary embodiment, the input device is a lever or thumbswitch that can be moved to correspond to the movement of a cutting element on the catheter. Thus, as the lever is moved proximally, the cutter is rotated and moved proximally to an open position. When the lever is moved to a distal position, the rotation of the cutter can be stopped and the cutter can be moved distally to pack severed tissue into a collection chamber.

Figure 21:
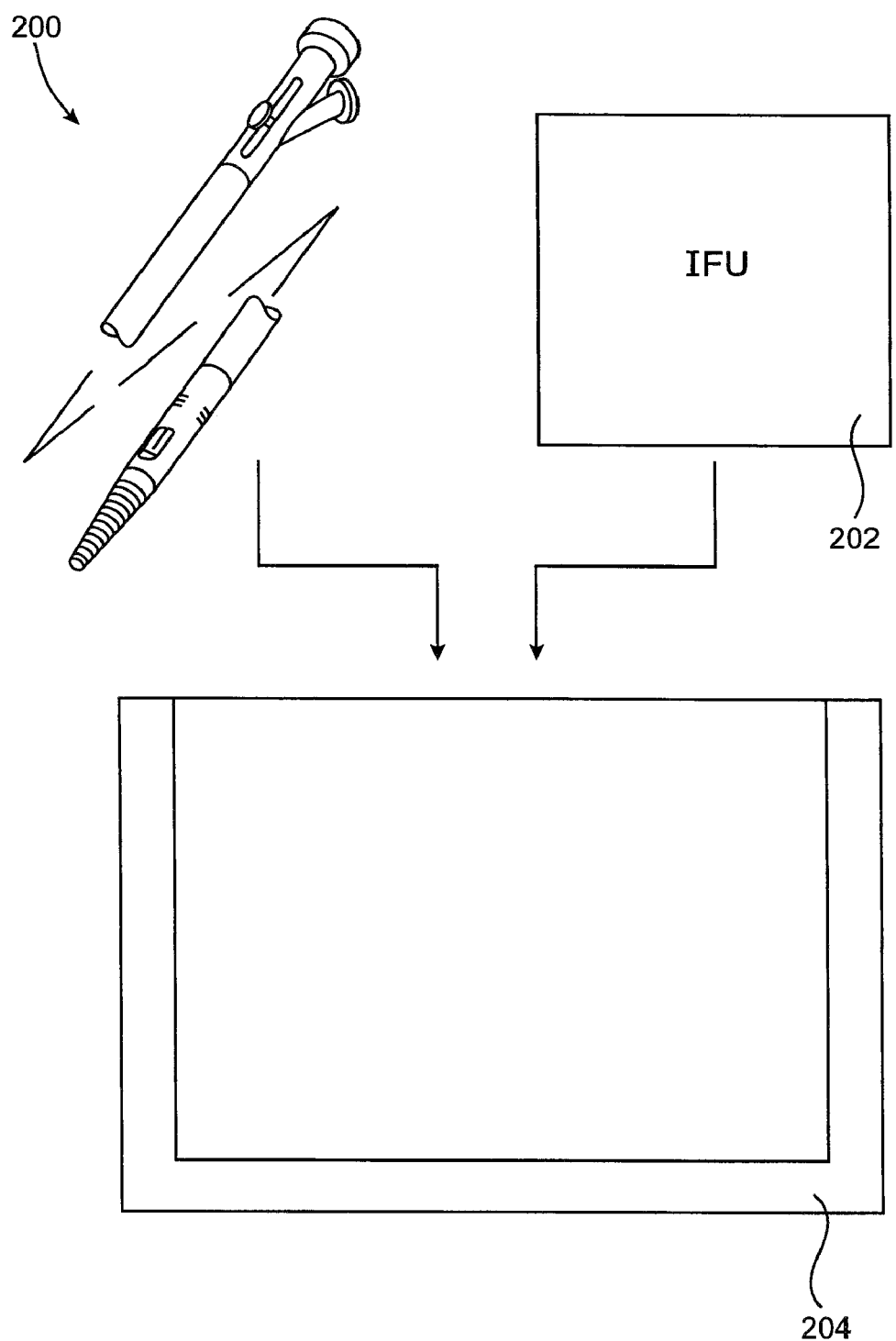
FIG. 21 illustrates a kit of the present invention.

Referring now to FIG. 21, the present invention will further comprise kits including catheters 200, instructions for use 202, and packages 204. Catheters 200 will generally be as described above, and the instruction for use (IFU) 202 will set forth any of the methods described above. Package 204 may be any conventional medical device packaging, including pouches, trays, boxes, tubes, or the like. The instructions for use 202 will usually be printed on a separate piece of paper, but may also be printed in whole or in part on a portion of the packaging 204.

While all the above is a complete description of the preferred embodiments of the inventions, various alternatives, modifications, and equivalents may be used. For example, while preferred cutters are moved proximally to move the cutter out of the cutting window, alternative embodiments may move the cutter distally to move the cutter out of the cutting window. Additionally, while most embodiments employ a cutter that extends out beyond the outer diameter of the cutting window, it may be possible to incorporate a cutter that stays within the diameter catheter body. Additionally, in some embodiments, the debulking assembly may be exposed through the window without causing a deflection of the distal portion of the catheter. Moreover, instead of having a distal tip that is rotatable relative to the proximal portion of the catheter, the catheter can include a shape memory material such that the catheter forms a jog or a pre-bent shape when it reaches its target area. Although the foregoing invention has been described in detail for purposes of clarity of understanding, it will be obvious that certain modifications may be practiced within the scope of the appended claims.

What is claimed is:

1. A method of removing material from a body lumen, the method comprising:

delivering a catheter comprising a tissue debulking device to a target site in the body lumen;

deflecting a distal portion of the catheter relative to a proximal portion of the catheter to expose the tissue debulking device through a cutting window, the deflecting step being carried out by sliding the tissue debulking device against a cam surface to expose the tissue debulking device through the cutting window; and debulking the body lumen by rotating the tissue debulking device about a first axis with the tissue debulking device being exposed through the cutting window in the catheter, the debulking step being carried out by advancing the catheter in the body lumen to move the rotating tissue debulking device and cutting window through material in the body lumen during the debulking step.

2. The method of claim 1 wherein the first axis is a longitudinal axis of the catheter.

3. The method of claim 1 further comprising packing severed material into a collection chamber.

4. The method of claim 1 wherein deflecting comprises urging the tissue debulking device against the material in the body lumen.

5. The method of claim 1 wherein delivering comprises attaching a guidewire to a monorail delivery assembly on the catheter.

6. The method of claim 1 wherein the target site is a stent.

7. The method of claim 1 wherein deflecting is carried out by moving the tissue debulking device from a first position to a second position.

* * * * *